US006072030A

United States Patent [19]
Bombardelli et al.

[11] Patent Number: 6,072,030
[45] Date of Patent: *Jun. 6, 2000

[54] HYDROXYPROLINE-RICH PROTEINS AND PHARMACEUTICAL AND COSMETIC FORMULATIONS CONTAINING THEM

[75] Inventors: Ezio Bombardelli; Cesare Ponzone, both of Milan, Italy

[73] Assignee: Indena S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/849,866
[22] PCT Filed: Dec. 21, 1995
[86] PCT No.: PCT/EP95/05084
  § 371 Date: Jun. 18, 1997
  § 102(e) Date: Jun. 18, 1997
[87] PCT Pub. No.: WO96/20284
  PCT Pub. Date: Jul. 4, 1996

[30] Foreign Application Priority Data

Dec. 28, 1994 [IT] Italy .................. MI94A2663

[51] Int. Cl.[7] ...................................... C07K 5/00
[52] U.S. Cl. .......................... 530/350; 530/324; 424/401; 424/455; 424/451; 514/8
[58] Field of Search ....................... 424/401, 455, 424/451; 514/8; 530/300, 324, 350, 356, 353, 370, 379

[56] References Cited

U.S. PATENT DOCUMENTS 5,443,855  8/1995  Wolf et al. ............... 424/401

FOREIGN PATENT DOCUMENTS 0 533 408  3/1993  European Pat. Off. .

OTHER PUBLICATIONS

J.P. Stafstrom et al., "A Second Extensin–Like Hydroxyproline–Rich Glycoprotein From Carrot Cell Walls", *Plant Physiol.*, vol. 84 (1987) pp. 820–825.
Schmidt et al Plant. Physiol. vol. 96 p. 656, Nov. 1990.
Chen et al, PNAS, vol. 82 p. 4399, Jul. 1985.

*Primary Examiner*—Sheela Huff
*Attorney, Agent, or Firm*—Pennie & Edmonds LLP

[57] ABSTRACT

The invention relates to hydroxyproline-rich glycoproteins, which can be obtained by acid alcohol extraction from Taxus supp., *Gingko biloba, Lycopersicum esculentum* and *Daucus carota* cell cultures, having the following characteristics: average molecular weight 20,000 Daltons with variability interval 12,000 to 38,000, determined by means of gel permeation and electrophoresis; high solubility in water.

7 Claims, No Drawings

HYDROXYPROLINE-RICH PROTEINS AND PHARMACEUTICAL AND COSMETIC FORMULATIONS CONTAINING THEM

TECHNICAL FIELD

The present invention relates to hydroxyproline-rich glycoproteins which can be obtained from vegetable sources, and to the pharmaceutical and cosmetic use thereof.

More precisely, the invention relates to hydroxyproline-rich glycoproteins, which can be obtained by acid alcohol extraction from Taxus spp., *Gingko biloba, Lycopersicum esculentum* and *Daucus carota* cell cultures, having the following characteristics:

average molecular weight 20,000 Daltons with variability interval 12,000 to 38,000, determined by means of gel permeation and electrophoresis;

solubility in acid aqueous solutions.

Some glycoproteins of animal origin, such as collagen and proteoglycans, are known to exert a beneficial action on the skin when applied topically as such or incorporated in suitable formulations.

BACKGROUND ART

Collagen, which is a glycoprotein rich in proline and hydroxyproline, is especially used as such or combined with other polypeptide bases in the treatment of wrinkles and other unaesthetic blemishes linked to poor skin hydration and elasticity. The animal origin of collage, however, limits its use because of the risks of contamination from viruses and toxins. Though the compounds of vegetable origin do not involve these risks, so far their use in cosmetics has been quite limited: for examples, cosmetic formulations are known which contain raw extracts of such plants as Aloe or even entire minced vegetables such as avocado.

Vegetable glycoproteins, called extensines, that are produced from vegetable cells in the proliferation stage and have a similar structure to animal collagen, are known. EP-A-0 533 4078 discloses the cosmetic use of extensines having an average molecular weight above 100,000 Daltons. However, the methods for the extraction of extensines described to date, which involve the extraction of vegetable materials of various origin by means of aqueous saline solutions, followed by purification with strong acids such as trichloroacetic acid, do not allow to obtain suitable products for cosmetics, due to problems concerning solubility, stability, repeatability and consistency of their chemical-physical characteristics.

SUMMARY OF THE INVENTION

It has now been found that it is possible to obtain hydroxyproline-rich glycoproteins, structurally similar to the above described extensines but with a lower molecular weight and a higher solubility in acid aqueous solutions, by means of a procedure comprising the in vitro culture of cells of selected plants and the extraction, with acid alcoholic solutions, of the cells grown in a suitable medium.

DETAILED DESCRIPTION OF THE PREFERRED EMBODIMENTS

The glycoproteins obtainable according to the invention have hydrating, film-forming, toning and cicatrizant properties higher than those of collagen. The glycoproteins of this invention can therefore be employed in cosmetic or dermatologic formulations for the treatment of dry skin, psoriasis, ichtyosis, dandruff, keratosis, wrinkles, acne, eczema, inflammatory dermatosis, ageing of the skin and all the other applications for which the use of animal collagen has been proposed.

The aqueous solutions of the glycoproteins of the invention remain stable without any polymerisation of the glycoproteins leading to the formation of insoluble products. In addition, the viscosity of these solutions is particularly high and not dependent on the concentrations; 0.1% concentrations surprisingly have the same film-forming and hydrating power equal as 1% collagen or 5% vegetable albumin solutions.

The vegetable material to be extracted is obtained from fermenter cultures of Taxus spp., *Gingko biloba, Lycopersicum esculentum* and *Daucus carota* cells. The use of cells from the species Taxus spp., *Gingko biloba* and *Lycopersicum esculentum* is particularly preferred. The cell culture techniques are conventional and include the suspension culture starting from callus cultures from various parts of the plants such as leaves, bark, roots, trunk or seeds, as described by Dobbs and Roberts, Experiments in Plant Tissue Culture, 2nd ed. Cambridge University Press, New York, 1985.

The vegetable tissue of the callus, following sterilisation and optional addition of antibacterials, is typically used for the inoculum of suitable liquid culture media as described in the above mentioned Manual by Dobbs and Roberts. A particularly suitable medium for this invention is the Murashige and Skoog medium. The addition of specific additives such as proline, reducing agents, ethylene or compounds capable of releasing ethylene such as Ethephon or L-aminocyclo-propanecarboxylic acid, may be suitable to increase productivity in the desired glycoproteins.

The use of naphthylacetic acid as the as auxin, 6-($\gamma,\gamma$-dimethylamino)-purine as the cytokinin, vitamins and 3% saccharose as the carbon source is preferred. The addition of vitamin C may be suitable, depending on the material chosen, to prevent the final product from browning.

The fermentation time may vary from 3 to 12 days and is preferably between 5 and 6 days. Once the fermentation has been completed, the culture medium is centrifuged and the cellular mass is extracted by means of alcohols, preferably ethanol, in the presence of diluted mineral acids, preferably hydrochloric or sulphuric acid. This procedure inactivates some enzymes that may jeopardise the stability of the glycoproteins of the invention, specifically of polyphenoloxidase and tyrosine oxidase which favour the polymerization of glycoproteins with the consequent formation of insoluble products.

The alcohol extraction in the presence of mineral acids allows the complete extraction of basic glycoproteins and has proved to be extremely selective to this end. Other water-mixable alcohols, such as methanol or isopropanol, can be used besides ethanol. The resulting hydroalcoholic extracts are neutralised and then concentrated and heated to a temperature of 70° C. to 100° C., preferably around 80° C., up to complete precipitation of the denatured proteins. The suspension is then clarified by concentration and the fluid is subjected to fractional ultrafiltration to remove high and low molecular weight substances. Ultrafiltration is performed by means of polysulphonic membranes having cut-off of 10,000 Daltons to 40,000 Daltons, such as Centricon$^R$ or Romicon$^R$, whose fibres may be hollow or, alternatively, coiled. The resulting filtered product is electrodialysed to remove undesired substances such as salts and low molecular weight sugars. After filtration and dialysis, the resulting solution can be used as such in cosmetic or pharmaceutical preparations or it can be concentrated to a lower volume and then lyophilised or atomised.

The analytical characterization of the products of the invention was carried out by gel permeation using a high-pressure liquid chromatograph consisting of a Waters pump unit and provided with a Ultrahydrogel Linear Waters[R] column battery 30 cm×0.5 cm and Waters UV absorption detector, model 484. An aqueous solution containing 0.067 M monopotassium phosphate, 0.1 M NaCl and 6×10$^{-4}$ M NaN$_3$ was used as the eluent. The glycoprotein samples to be analysed are dissolved in the same eluent solution (3 mg/10 ml) and scalar amounts of the substance as well as the reference substances selected as molecular weights between Cytochrome C (12,400 Daltons) and dextran blue (2,000,000 Daltons); alternatively or simultaneously the products or their intermediates can be determined by electrophoresis on 12.5% polyacrylamide gel and 4% stacking gel. The samples to be analysed are dissolved in a buffer containing SDS and 0.1% mercaptoethanol while depositing quantities between 100 mg and 300 mg. The migration is carried out at a constant current at 20 mA for 4 hours. A gauging curve is drawn with 5 standard weights (7 kD, 14 kD, 24 kD, 54 kD and 66 kD). Weights of 22.5 kD and 25 kD are calculated from this gauging curve for the two main bands and weights of 31 kD and 34 kD are calculated for the less intense bands. The procedures described here allow mixtures of products with comparable molecular weights and comparable amino acid compositions to be obtained from the various cell explants starting from different plants. The results of the amino acid analysis of glycoproteins extracted from *Ginkgo biloba* cells are shown below as an example.

| Amino acid | Peak area % |
|---|---|
| Asp | 4.399 |
| Glu | 4.328 |
| Hyp | 17.505 |
| Ser | 7.065 |
| Gly | 6.056 |
| Hys | 1.782 |
| Arg | 2.471 |
| Thr | 4.739 |
| Pro | 10.036 |
| Ala | 8.2 |
| Tyr | 2.388 |
| Val | 6.162 |
| Met | 1.154 |
| Ile | 2.479 |
| Leu | 5.525 |
| Phe | 1.862 |
| Lys | 14.254 |

The above data refer to the percentage of the total amount of amino acids present in the glycoprotein mixture. The sugars in the mixture are arabinose and galactose. The ratio of amino acids to sugars is on average 2:1 for the various products.

As mentioned above, the products according to the invention can be used both in the pharmaceutical and cosmetic fields. For the pharmaceutical field, the product may be incorporated in gels or ointments or applied on medicated gauzes for specific treatment of burns or wounds. In this case the product is usually subjected to sterilisation or sterile filtrations and lyophilised.

The cosmetic and dermatologic preparations of the invention can be prepared according to traditional methods. Examples of administration forms include aqueous sprays, lotions, solutions, emulsions, gels, ointments and creams.

The cosmetic and dermatologic preparations of the inventions can contain hydroxyproline-rich glycoproteins in weight percentages of about 0.01% to about 50%, preferably from 0.05% to 5%, as well as conventional excipients. Given the high stability of the glycoproteins of this invention, pharmaceutical and cosmetic preparations containing above 50% of soluble hydroxyproline-rich glycoproteins can be obtained.

The glycoproteins of the invention can be added to pharmaceutical and cosmetic preparations as such or microencapsulated so as to provide a long-term hydrating action. The microcapsules can be either hydrophilic or lipophilic. The preparations of the invention may include other active principles having complementary or useful activity for the desired aims.

EXAMPLES

The invention is further illustrated by the following examples.

Example 1

Preparation of the callus and liquid culture of *Ginkgo biloba* for the production of glycoproteins An explant of young leaves of *Ginkgo biloba* is prepared by washing the leaves in a 0.1% Tween $_{80}$[R] solution. The laminae are sectioned in fractions of about 0.5 cm and pre-sterilised for 1 minute with 75% ethanol. The sterilisation is then completed with a 2% sodium hypochlorite solution and triple washing of the explant in sterile water. The resulting explants are transferred to a Petri dish in Murashige & Skoog medium containing 3% saccharose with the addition of Lynsmeyer & Skoog vitamins and hormones such as 2,4-dichlorophenoxyacetic acid and naphthylacetic acid. The products are incubated in the dark at 23° C. for 20 days. At the end of this period, friable calli are obtained which grow easily and are moved in continuous rows by means of subcultures in the same conditions, as they can be used for propagation in a liquid medium. These calli are used to inoculate Erlenmeyer flasks containing 200 ml of Murashige & Skoog medium, with the addition of naphthylacetic acid and 6 (γ,γ-dimethylamino)-purine, Lynsmeyer & Skoog vitamins and 3% saccharose as a source of carbon. The flasks are incubated with stirring in continuous light for 4 days, after which the cell biomass is harvested for the extraction of glycoproteins.

Example 2

Preparation of glycoproteins from *Ginkgo biloba* cells 5 liters of the culture obtained according to Example 1 are low-speed centrifuged and the harvested cells (1.5 kg of fresh weight) are extracted with 1.5 l of 70% ethanol containing 1% sulphuric acid. The extraction is repeated twice thereby quantitatively recovering the basic glycoproteins. After neutralisation, the extracts are filtered to remove any turbidity and concentrated under vacuum at 50° C. until ethanol is completely removed. The aqueous concentrate is heated at 85° C. for 30 minutes and centrifuged again to remove the precipitate, which is discarded. The resulting clear solution is ultrafiltered by means of a Centricon[R] membrane with cut-off 40,000 Dalton limit to exclude the higher molecular weights.

The filtered product is then ultrafiltered using a hollow-fibre membrane with cut-off 10,000 Dalton to remove non-glycoprotein, low-molecular weight substances. The filtrate is then subjected to dialysis and concentrated to 1% of solid residue. 1.5 liters of a slightly viscous product is obtained, which may be used as such in cosmetic formulations. At the electrophoresis analysis, the product contained 6 bands, 4 of which had molecular weights of 16,000, 22,000, 33,000 and 36,000 Daltons.

Example 3

Preparation of glycoproteins from *Lycopersicum esculentum*

Following the procedure of Example 1, a cell mass from sterile buds of *Lycopersicum esculentum* is prepared in a 14-liter fermenter containing 10 liters of Murashige & Skoog medium added with naphthylacetic acid and 6 (γ,γ-dimethylamino)-purine, Lynsmeyer & Skoog vitamins and 3% saccharose as a carbon source. The fermentation is carried on for 5 days at 23° C. while stirring at 150 rpm in the presence of yeast extract at 0.05% concentration and with an approximately 70% concentration of dissolved oxygen. At the end of the fermentation the broth is gathered and micro-filtered through a 0.2 μm ceramic membrane to concentrate the cells. Some isopropanol containing 0.5% hydrochloric acid is added to the cell paste thus obtained and the method described in Example 2 is applied to the extracts. 3.5 liters of a solution are obtained with 0.5% dry residue. The analysis of the lyophilised solutions gave a content of 10% proline and 31% hydroxyproline, respectively.

Example 4

| Cosmetic formulation | |
| --- | --- |
| 100 g of O/W emulsion contain: | |
| SOLUTION OF THE EXAMPLE 2 OR 3 | 10.0 g |
| Acetylated lanolin alcohol PEG-10 | 2.0 g |
| Cetyl-stearyl alcohol | 1.5 g |
| Cetyl palmitate | 2.0 g |
| Stearic acid | 7.0 g |
| Octyl octanoate | 7.5 g |
| Potassium cetyl phosphate | 0.5 g |
| Preservatives | q.s. |
| Fragrance | q.s. |
| Purified water | q.s. to 100 g |

Example 5

| Cosmetic formulation | |
| --- | --- |
| 100 g of O/W emulsion contain: | |
| SOLUTION OF THE EXAMPLE 2 OR 3 | 10.0 g |
| Cetyl stearyl glucoside | 5.0 g |
| Jojoba oil | 10.0 g |
| Isopropyl myristate | 8.0 g |
| Dimethicone | 0.5 g |
| Antioxidant | q.s. |
| Preservatives | q.s. |
| Fragrance | q.s. |
| Purified water | q.s. to 100 g |

What is claimed is:

1. A method for obtaining hydroxyproline-rich glycoproteins which comprises:
    a) culturing cells of *Gingko biloba* or *Lycopersicum esculentum* in a liquid culture medium for 3 to 12 days;
    b) extracting the cultured cells with an alcohol having one to three carbon atoms in the presence of a dilute acid material to obtain an extract;
    c) neutralizing, concentrating and heating the extract at a temperature of between 70° C. and 100° C.; and
    d) centrifuging the heated extract to obtain a supernatant and precipitate, discarding the precipitate, and subjecting the supernatant to fractional ultrafiltration and dialysis to obtain the hydroxyproline-rich glycoproteins.

2. Hydroxyproline-rich glycoproteins prepared by the process of claim 1, wherein said glycoproteins have an average molecular weight of 20,000 Daltons with a variable interval of 12,000 to 38,000 Daltons, as determined by SDS-Page under reducing conditions.

3. The hydroxyproline-rich glycoproteins of claim 2, wherein the glycoproteins are obtained from cell cultures of *Gingko biloba* or *Lycopersicum esculentum*.

4. A cosmetic or pharmaceutical preparation containing the hydroxyproline rich glycoproteins prepared by the process of claim 1.

5. A preparation according to claim 4 in the form of a lotion, solution, emulsion, gel, ointment, cream, or medicated gauze.

6. The method of claim 1 wherein the alcohol is methanol, ethanol or isopropanol.

7. The method of claim 1 wherein the cells are cultured for 5 to 6 days and the extract is heated to a temperature of about 80° C.

* * * * *